(12) United States Patent
Lalvani et al.

(10) Patent No.: US 7,901,898 B2
(45) Date of Patent: *Mar. 8, 2011

(54) TUBERCULOSIS DIAGNOSTIC TEST

(75) Inventors: Ajit Lalvani, Oxford (GB); Ansar Pathan, Oxford (GB)

(73) Assignee: Isis Innovation Limited, Summertown, Oxford (GB)

( * ) Notice: Subject to any disclaimer, the term of this patent is extended or adjusted under 35 U.S.C. 154(b) by 0 days.

This patent is subject to a terminal disclaimer.

(21) Appl. No.: 12/579,019

(22) Filed: Oct. 14, 2009

(65) Prior Publication Data

US 2010/0041075 A1   Feb. 18, 2010

Related U.S. Application Data

(63) Continuation of application No. 09/830,839, filed as application No. PCT/GB99/03635 on Nov. 3, 1999, now Pat. No. 7,632,646.

(60) Provisional application No. 60/107,004, filed on Nov. 4, 1998.

(30) Foreign Application Priority Data

Nov. 4, 1998 (GB) .................................. 9824213.4

(51) Int. Cl.
 G01N 33/53 (2006.01)
 G01N 33/567 (2006.01)
 G01N 33/554 (2006.01)
 G01N 33/569 (2006.01)

(52) U.S. Cl. .......... 435/7.1; 435/7.2; 435/7.32; 435/975; 530/300

(58) Field of Classification Search .................. None
See application file for complete search history.

(56) References Cited

U.S. PATENT DOCUMENTS

| | | | |
|---|---|---|---|
| 5,736,524 A | 4/1998 | Content et al. | |
| 5,955,077 A | 9/1999 | Andersen et al. | |
| 6,245,331 B1 | 6/2001 | Laal et al. | |
| 6,290,969 B1 | 9/2001 | Reed et al. | |
| 6,338,852 B1 | 1/2002 | Reed et al. | |
| 6,350,456 B1 | 2/2002 | Reed et al. | |
| 6,384,018 B1 | 5/2002 | Content et al. | |
| 6,458,366 B1 | 10/2002 | Reed et al. | |
| 6,537,552 B1 | 3/2003 | Minion et al. | |
| 6,596,281 B1 | 7/2003 | Gennaro et al. | |
| 6,613,881 B1 | 9/2003 | Alderson et al. | |
| 6,641,814 B1 | 11/2003 | Andersen et al. | |
| 6,649,170 B1 | 11/2003 | Lindblad et al. | |
| 6,673,353 B1 | 1/2004 | Kaufmann et al. | |
| 6,776,993 B2 | 8/2004 | Kaufmann et al. | |
| 6,962,710 B2 | 11/2005 | Reed et al. | |
| 6,982,085 B2 | 1/2006 | Andersen et al. | |
| 6,991,797 B2 | 1/2006 | Andersen et al. | |
| 7,037,510 B2 | 5/2006 | Andersen et al. | |
| 7,087,713 B2 | 8/2006 | Campos-Neto et al. | |
| 7,115,361 B2 * | 10/2006 | Lalvani et al. | ..................... 435/4 |
| 7,122,196 B2 | 10/2006 | Reed et al. | |
| 7,135,280 B2 | 11/2006 | Lalvani | |
| 7,238,358 B2 | 7/2007 | Reed et al. | |
| 7,261,897 B2 | 8/2007 | Skeiky et al. | |
| 7,393,539 B2 | 7/2008 | James et al. | |
| 7,572,597 B2 * | 8/2009 | Lalvani et al. | ............... 435/7.32 |
| 7,575,870 B1 | 8/2009 | Lalvani et al. | |
| 7,632,646 B1 * | 12/2009 | Lalvani et al. | ................. 435/7.1 |
| 7,785,607 B2 * | 8/2010 | Goletti et al. | .............. 424/248.1 |
| 7,811,588 B2 * | 10/2010 | James et al. | ............... 424/248.1 |
| 2002/0094336 A1 | 7/2002 | Andersen et al. | |
| 2002/0131976 A1 | 9/2002 | Lalvani et al. | |
| 2003/0044431 A1 | 3/2003 | Schurig et al. | |
| 2004/0115211 A1 | 6/2004 | Andersen et al. | |
| 2006/0019323 A1 | 1/2006 | Leclerc et al. | |
| 2006/0115847 A1 | 6/2006 | Andersen et al. | |
| 2006/0121537 A1 | 6/2006 | Gahery-Segard et al. | |
| 2007/0036816 A1 | 2/2007 | Campos-Neto et al. | |
| 2007/0184073 A1 | 8/2007 | Andersen et al. | |
| 2008/0008724 A1 | 1/2008 | Aagaard et al. | |
| 2008/0124738 A1 | 5/2008 | Green | |
| 2008/0267990 A1 | 10/2008 | Andersen et al. | |
| 2008/0311159 A1 * | 12/2008 | Klein et al. | ................. 424/248.1 |
| 2009/0074803 A1 | 3/2009 | Sallberg et al. | |
| 2009/0136534 A1 | 5/2009 | Shafferman et al. | |
| 2010/0159485 A1 * | 6/2010 | Mukhopadhyay et al. | .. 435/7.32 |

FOREIGN PATENT DOCUMENTS

| | | |
|---|---|---|
| EP | 1152012 | 7/2007 |
| WO | WO9501441 | 1/1995 |
| WO | WO9816646 | 4/1998 |
| WO | WO9823960 | 6/1998 |
| WO | WO9945119 | 9/1999 |
| WO | WO02154072 | 7/2002 |
| WO | WO 2008/032092 A1 * | 3/2008 |

OTHER PUBLICATIONS

Lalvani et al, Eur. Resp. J. 2008, 32/6:1428-1430.*
Dinnes et al, Health Technology Assessment, Jan. 2007, 11/3:1-178 abstract only.*
Harada, Kekkaku, Nov. 2006, 81/11:681-686 abstract only.*
Ruhwald et al, Expt. Rev. Resp. Med., Aug. 2009, 3/4:387-401 abstract only.*
U.S. Appl. No. 09/830,839, filed Feb. 19, 2002, Lalvani et al.
Andersen, Trends in Immunology, Mar. 2001, 22/3:160-168.
Arend et al., J. Infectious Diseases, 2000, 181:1850-1854.
Bixler et al., in: Synthetic Vaccines, vol. 1, Editor: Arnon, 1987, pp. 39-71.
Bowie et al., Science, Mar. 1990, 247:1306-1310.
Brandt, et al., "Key Epitopes on the ESAT-6 Antigen Recognized in Mice During the Recall of Protective Immunity to Mycobacterium Tuberculosis", J. Immunol., vol. 1996, No. 157, 1996. p. 3527-3533.
Brodin et al., Trends in Microbiology, Nov. 2004, 12/11:500-508.
Buddle et al., Vet. Microbiology, 2001, 80:37-46.

(Continued)

Primary Examiner — N. M Minnifield
(74) Attorney, Agent, or Firm — Baker Botts L.L.P.

(57) ABSTRACT

A method of diagnosing in a host infection by or exposure to a mycobacterium which expresses ESAT-6 comprising (i) contacting a population of T cells from the host with one or more peptides or analogues selected from the peptides represented by SEQ ID NO:1 to 11 and analogues thereof which can bind a T cell receptor which recognises any of the said peptides, and (ii) determining whether the T cells of said T cell population recognise the peptide(s) and/or analogue(s). The method may performed in vivo. Peptides and a kit which enable the method to be carried out are provided.

19 Claims, No Drawings

OTHER PUBLICATIONS

Burgess et al., J. Cell Biology, Nov. 1990, 111:2129-2138.
Chothia et al., The EMBO Journal, 1986, 5/4: 823-826.
Demissie et al., Infection and Immunity, Nov. 1999, 67/11:5967-5971.
Elhay, M.J. et al., "Delayed-Type Hypersensitity Responses to ESAT-6 and MPT64 from Mycobacterium Tuberculosis in the Guinea Pig", Infect Immun., vol. 66, No. 7, Jul. 1998, p. 3454-3456.
Geluk et al., Infection and Immunity, May 2002, 70/5:2544-2548.
Glatmen-Freedman et al., Clinical Microbiology Reviews, Jul. 1998, 11/3:514-532.
Greenspan et al., Nature Biotechnology, Oct. 1999, 17:936-937.
Harboe, M. et al., "B-Bell Epitopes and Quantification of the ESAT-6 Protein of Mycobacterium Tuberculosis", Infect. Immun., vol. 66, No. 2, Feb. 1998, p. 717-723.
Houghten et al., Vaccines 86, 1986, Editors: Brown et al., pp. 21-25.
International Search Report, Apr. 19, 2000, PCT/GB1999/03635, International Filing Date—Nov. 3, 1999.
Kanaujia et al., Clin. Diagn. Lab. Immunol., Jan. 2004, 11/1:222-226.
Kumar et al., PNAS, USA, Feb. 1990, 87:1337-1341.
Lalvani & Hill, (1998), MRS Meeting of May 15, 1997, Royal College of Physicians London, Clinical Science 95, 531-538.
Lalvani et al. (Jan. 1998) Proc. Natl. Acad. Sci. USA 95, 270-275.
Lalvani et al., Am. J. Respiratory Critical Care Medicine, 2001, 163:824-828.
Lalvani et al., J. Infectious Diseases, 2001, 183:469-477.
Lazar et al., Molecular and Cellular Biology, Mar. 1988, 8/3:1247-1252.
Lowrie et al., BioDrugs, 1998, 10/3:201-213.
Lowrie et al., Springer Seminars in Immunopathology, 1997, 19:161-173.
Minion et al., Infection and Immunity, Apr. 2003, 71/4:2239-2243.
Mollenkopf et al., Vaccine, 2001, 19:4028-4035.
Morris et al., Vaccine, 2000, 18:2155-2163.
Mustafa et al., Clinical Infectious Diseases, 2000, 30/Suppl. 3:S201-S205.
Mustafa et al., Scandinavian J. Immunology, 2003, 57:125-135.
Mustafa, Molecular Immunology, 2002, 39:113-119.
Olsen et al., Eur. J. Immunol., Jun. 2000, 30/6:1724-1732; Abstract only.
Pathan, A. et al., "Human T-Cell Responses to the Antigen ESAT-6 Cgaracteruze a Vacube Candidate and Potential Diagnostic Test for Tuberculosis", Immunology, vol. 95, No. Suppl. 1, Dec. 1998, p. 90.
Pathan, A. et al., "Identification of Conserved CD8+ Cytotoxic T Cell Epitopes in ESAT-6, a Tuberculosis Vaccine Candidate", Immunology, vol. 95, No. Suppl. 1, Dec. 1998, p. 108.
Pollock & Anderson (1997) J. Infect. Diseases 175, 1251-1254.
Rhodes et al., Infection and Immunity, May 2000, 68/5:2573-2578.
Saleem et al., J. Controlled Release, 2005, 102:551-561.
Scarpellini et al., J. Clinical Microbiology, Aug. 2004, 42/8:3469-3474.
Sinha et al., Comparative and Functional Genomics, 2002, 3:470-483.
Skjot et al., Infection and Immunity, Jan. 2000, 68/1:214-220.
Skjot et al., Infection and Immunity, Oct. 2002, 70/10:5446-5453.
Skjot et al., Scand. J. Infectious Disease, 2001, 33:643-647.
Sorenson et al. (1995) Infect. Immun. 63, 1710-1717.
Spencer et al., Infection and Immunity, Feb. 2002, 70/2:1010-1013.
Thorn et al., Vet. Immunol. and Immunopathol., 2004, 103:399-412.
Trajkovic et al., Microbes and Infections, 2004, 6:513-519.
Ulrichs et al., International J. tuberculosis and Lung Disease, 2000, 4/12:1181-1183.
Ulrichs, T. et al., "Differential T Cell Responses to Mycobacterium Tuberculosis ESAT-6 in Tuberculosis Patients and Healthy Donors", Eur. J. Immunol., vol. 28, No. 12, Dec. 1998, p. 3949-3958.
van Pinxteren et al., Clinical and Diagnostic Laboratory Immunology, Mar. 2000, 7/2:155-160.
van Pittius et al., Infection and Immunity, Nov. 2002, 70/11:6509-6511.
Vekemans et al., Infection and Immunity, Oct. 2001, 69/10:6554-6557.
Vincenti et al., Mol. Med., Mar.-Apr. 2003, 9/3-4:105-111; Abstract only.
Vordermeier et al., Clinical and Diagnostic Laboratory Immunology Sep. 1999, 6/5:675-682.
Vordermeier et al., Clinical and Diagnostic Laboratory Immunology, May 2001, 8/3:571-578.
Vordermeier et al., Clinical Infectious Diseases, 2000, 30 (Suppl. 3):S291-S298.
Vordermeier et al., Eur. Respir. J., 1995, 8/Suppl. 20:657s-667s.
Vordermeier et al., Infection and Immunity, Apr. 2003, 71/4:1980-1987.
U.S. Appl. No. 09/830,839, filed Apr. 30, 2001, Preliminary Amendment at Filing.
U.S. Appl. No. 09/830,839, filed Apr. 22, 2003, Requirement for Restriction/Election.
U.S. Appl. No. 09/830,839, filed May 16, 2003, Response to Restriction/Election.
U.S. Appl. No. 09/830,839, filed Aug. 4, 2003, Non-Final Rejection.
U.S. Appl. No. 09/830,839, filed Nov. 19, 2003, Response to Non-Final Rejection.
U.S. Appl. No. 09/830,839, filed Feb. 27, 2004, Non-Final Rejection.
U.S. Appl. No. 09/830,839, filed May 12, 2004, Response to Non-Final Rejection.
U.S. Appl. No. 09/830,839, filed Jul. 27, 2004, Final Rejection.
U.S. Appl. No. 09/830,839, filed Sep. 27, 2004, Response to Final Rejection.
U.S. Appl. No. 09/830,839, filed Jan. 5, 2005, Advisory Action mailed.
U.S. Appl. No. 09/830,839, filed Apr. 8, 2005, Non-Final Rejection.
U.S. Appl. No. 09/830,839, filed Aug. 4, 2005, Response to Non-Final Rejection.
U.S. Appl. No. 09/830,839, filed Nov. 7, 2005, Final Rejection.
U.S. Appl. No. 09/830,839, filed Apr. 7, 2006, Response to Final Rejection with RCE filed.
U.S. Appl. No. 09/830,839, filed Jun. 29, 2006, Non-Final Rejection.
U.S. Appl. No. 09/830,839, filed Sep. 28, 2007, Response to Non-Final Rejection.
U.S. Appl. No. 09/830,839, filed Jan. 16, 2009, Final Rejection.
U.S. Appl. No. 09/830,839, filed May 18, 2009, Response After Final Rejection with RCE filed.
U.S. Appl. No. 09/830,839, filed Jul. 2, 2009, Notice of Allowance mailed.
U.S. Appl. No. 09/830,839, filed Oct. 2, 2009, Amendment After Notice of Allowance.
Surcel HM, et al., "Th1/Th2 profiles in tuberculosis, based on the proliferation and cytokine response of blood lymphocytes to mycobacterial antigens," Immunology. Feb. 1994;81(2):171-6.
Ravn P et al., "Human T cells responses to the ESAT-6 antigen from Mycobacterium tuberculosis," The Journal of Infectious Diseases (1999);179:637-45.

* cited by examiner

SEQUENCE LISTING

<160> NUMBER OF SEQ ID NOS: 11

<210> SEQ ID NO 1
<211> LENGTH: 15
<212> TYPE: PRT
<213> ORGANISM: Mycobacterium tuberculosis

<400> SEQUENCE: 1

Met Thr Glu Gln Gln Trp Asn Phe Ala Gly Ile Glu Ala Ala Ala
 1               5                  10                  15

<210> SEQ ID NO 2
<211> LENGTH: 15
<212> TYPE: PRT
<213> ORGANISM: Mycobacterium tuberculosis

<400> SEQUENCE: 2

Ser Ala Ile Gln Gly Asn Val Thr Ser Ile His Ser Leu Leu Asp
 1               5                  10                  15

-continued

<210> SEQ ID NO 3
<211> LENGTH: 15
<212> TYPE: PRT
<213> ORGANISM: Mycobacterium tuberculosis

<400> SEQUENCE: 3

Gln Lys Trp Asp Ala Thr Ala Thr Glu Leu Asn Asn Ala Leu Gln
 1               5                  10                  15

<210> SEQ ID NO 4
<211> LENGTH: 15
<212> TYPE: PRT
<213> ORGANISM: Mycobacterium tuberculosis

<400> SEQUENCE: 4

Asn Asn Ala Leu Gln Asn Leu Ala Arg Thr Ile Ser Glu Ala Gly
 1               5                  10                  15

<210> SEQ ID NO 5
<211> LENGTH: 15
<212> TYPE: PRT
<213> ORGANISM: Mycobacterium tuberculosis

<400> SEQUENCE: 5

Asn Leu Ala Arg Thr Ile Ser Glu Ala Gly Gln Ala Met Ala Ser
 1               5                  10                  15

<210> SEQ ID NO 6
<211> LENGTH: 15
<212> TYPE: PRT
<213> ORGANISM: Mycobacterium tuberculosis

<400> SEQUENCE: 6

Trp Asn Phe Ala Gly Ile Glu Ala Ala Ala Ser Ala Ile Gln Gly
 1               5                  10                  15

<210> SEQ ID NO 7
<211> LENGTH: 15
<212> TYPE: PRT
<213> ORGANISM: Mycobacterium tuberculosis

<400> SEQUENCE: 7

Glu Gly Lys Gln Ser Leu Thr Lys Leu Ala Ala Ala Trp Gly Gly
 1               5                  10                  15

<210> SEQ ID NO 8
<211> LENGTH: 15
<212> TYPE: PRT
<213> ORGANISM: Mycobacterium tuberculosis

<400> SEQUENCE: 8

Tyr Gln Gly Val Gln Gln Lys Trp Asp Ala Thr Ala Thr Glu Leu
 1               5                  10                  15

<210> SEQ ID NO 9
<211> LENGTH: 15
<212> TYPE: PRT
<213> ORGANISM: Mycobacterium tuberculosis

<400> SEQUENCE: 9

Asn Val Thr Ser Ile His Ser Leu Leu Asp Glu Gly Lys Gln Ser
 1               5                  10                  15

<210> SEQ ID NO 10

```
<211> LENGTH: 15
<212> TYPE: PRT
<213> ORGANISM: Mycobacterium tuberculosis

<400> SEQUENCE: 10

Ile Glu Ala Ala Ala Ser Ala Ile Gln Gly Asn Val Thr Ser Ile
  1               5                  10                  15

<210> SEQ ID NO 11
<211> LENGTH: 15
<212> TYPE: PRT
<213> ORGANISM: Mycobacterium tuberculosis

<400> SEQUENCE: 11

Thr Ala Thr Glu Leu Asn Asn Ala Leu Gln Asn Leu Ala Arg Thr
1               5                  10                  15
```

TUBERCULOSIS DIAGNOSTIC TEST

REFERENCE TO RELATED APPLICATIONS

This application is a continuation application of U.S. patent application Ser. No. 09/830,839, filed on Feb. 19, 2002, and issued as U.S. Pat. No. 7,632,646, which is a U.S. National Phase Application under 35 U.S.C. §371 of International Patent Application No. PCT/GB99/03635, filed Nov. 3, 1999, and published in English on May 11, 2000, as International Publication No. WO 00/26248, which claims priority benefit from Great Britain Application No. 9824213.4 filed Nov. 4, 1998, and U.S. Provisional Patent Application No. 60/107,004, filed Nov. 4, 1998, the contents of all of which are incorporated by reference herein.

SEQUENCE LISTING

The specification further incorporates by reference a substitute Sequence Listing submitted via EFS on Oct. 14, 2009. Pursuant to 37 C.F.R. §1.52(e)(5), the substitute Sequence Listing text file, identified as 0775290121.txt, is 2,788 bytes and was created on Oct. 14, 2009. The substitute Sequence Listing, electronically filed herewith, does not extend beyond the scope of the specification and thus does not contain new matter.

BACKGROUND

The invention relates to a method of diagnosis of mycobacterial infection, particularly *Mycobacterium tuberculosis* infection. It also relates to peptides and a kit which can be used to carry out the diagnostic method.

Current diagnostic tests for tuberculosis disease are either slow or unreliable. Tests that rely on the identification of the mycobacterium which causes tuberculosis are slow because culturing of the mycobacterium can take up to 8 weeks. In some cases it proves impossible to culture the bacteria. In addition the obtaining of samples to detect the presence of the mycobacterium often requires invasive procedures.

An alternative test is the tuberculin skin test (TST) or Mantoux test which is based on the detection of a delayed type hypersensitivity (DTH) response to an intradermal administration of a Purified Protein Derivative of the mycobacterium. Although this test takes less time than tests which rely on identification of the mycobacterium, it is less reliable because of the widespread use of BCG as a vaccine against tuberculosis. BCG is closely related to *M. tuberculosis* and therefore individuals who have been vaccinated with BCG can react positively to a TST. In addition a large proportion of people with active tuberculosis are not detected by a TST because of cutaneous immune anergy. Thus TST has a low specificity and sensitivity.

Using an assay which detects release of IFN-γ from T cells the inventors have found 8 peptides from the ESAT-6 protein of *M. tuberculosis* which are recognised by the T cells of a high proportion of patients with tuberculosis, and in particular the peptide represented by SEQ ID NO: 1 is recognised by 57% of patients tested and 68% of healthy contacts tested. These contacts have been exposed to open pulmonary tuberculosis. The inventors have combined these peptides into a panel of peptides which when used together in a diagnostic test provide a specificity of 91.5%, and a sensitivity of 96%. The inventors have also found three other peptides from ESAT-6 which are recognised by the T cells of patients with tuberculosis which can be used to increase the sensitivity of the diagnostic test.

Advantageously BCG does not have the ESAT-6 gene and therefore unlike previous tests, including TST, the diagnostic test can distinguish between patients with tuberculosis and patients who have been vaccinated with BCG.

Brandt et al. (1996), Journal of Immunology, 157, 3527-33 discloses epitopes from ESAT-6 which are recognised by mice. However it is not possible to predict based on the epitopes which are recognised in mice which epitopes will be recognised in humans. As well as other differences in epitope processing, presentation and recognition mice have different MHC molecules from humans, and thus are expected to recognise different epitopes from humans. This is demonstrated by the fact that Brandt et al find the recognition of epitopes in mice which are not found to be recognised in humans by the present inventors.

SUMMARY OF THE INVENTION

The invention provides a method of diagnosing infection in a host, or exposure of a host, to a mycobacterium which expresses ESAT-6 comprising (i) contacting a population of T cells from the host with one or more peptides or analogues selected from the peptides represented by SEQ ID NO: 1, 2, 3, 4, 5, 6, 7, 8, 9, 10 or 11, and analogues thereof which can bind a T cell receptor which recognises any of the said peptides, but not (a) SEQ ID NO: 3 or 5 or an analogue thereof alone, nor (b) a combination of peptides and/or analogues selected from SEQ ID NO: 3 and 5 and analogues thereof; and (ii) determining whether the T cells of said T cell population recognise the peptide(s) and/or analogue(s). Preferably at least the peptide represented by SEQ ID NO: 1 or an analogue thereof is used. In other preferred embodiments at least all of the peptides represented: by SEQ ID NO: 1, 5, 6 and 8; or by SEQ ID NO's 1 to 8 are used.

The invention also provides a kit for carrying out the method comprising one or more of the peptides or analogues and optionally a means to detect the recognition of the peptide by the T cell.

The invention additionally provides a peptide with the sequence of SEQ ID NO: 1, 2, 4, 6, 7, 8, 9, 10 or 11, or an analogue thereof, and a polynucleotide which is capable of being expressed to provide the peptide or analogue.

DETAILED DESCRIPTION OF THE INVENTION

The sequences of SEQ ID NOs 1 to 11 are shown below:

```
SEQ ID NO 1:      MTEQQWNFAGIEAAA  (ES 1)
SEQ ID NO 2:      SAIQGNVTSIHSLLD  (ES4)
SEQ ID NO 3:      QKWDATATELNNALQ  (ES12)
SEQ ID NO 4:      NNALQNLARTISEAG  (ES14)
SEQ ID NO 5:      NLARTISEAGQAMAS  (ES15)
SEQ ID NO 6:      WNFAGIEAAASAIQG  (ES2)
SEQ ID NO 7:      EGKQSLTKLAAAWGG  (ES7)
SEQ ID NO 8:      YQGVQQKWDATATEL  (ES11)
SEQ ID NO 9:      NVTSIHSLLDEGKQS  (ES5)
SEQ ID NO 10:     IEAAASAIQGNVTSI  (ES3)
SEQ ID NO 11:     TATELNNALQNLART  (ES13)
```

The host is generally a human but may be an animal, typically one which can be naturally or artificially infected by a mycobacterium. The host may be a mammal, such as a primate, cow, sheep, pig, badger or rodent, e.g. a mouse or rat. The host typically has an active or latent mycobacterial infection, or has had such an infection recently. The host may test positive or negative in a Mantoux test. The host may be at risk of a mycobacterial infection, typically for socio-economic reasons or may have a genetic or acquired predisposition to mycobacterial infection.

The host may be a healthy contact who has been exposed to a mycobacterium. Typically the exposure is to pulmonary tuberculosis, such as 'open' pulmonary tuberculosis which is sputum a. f. b. (acid-fast bacillus) smear positive. Thus the method may be used to trace the healthy contacts of individuals with such tuberculosis infections. The method may also be used to carry out population surveys to measure the number of individuals in a population who have a mycobacterial infection or are healthy contacts.

The mycobacterium expresses ESAT-6. Generally, the ESAT-6 has a sequence which comprises one or more of the sequences represented by SEQ ID NO: 1, 2, 3, 4, 5, 6, 7, 8, 9, 10 or 11 or one or more homologues of these sequences. Such homologues can bind a T cell receptor which recognises the equivalent peptide represented by SEQ ID NO: 1, 2, 3, 4, 5, 6, 7, 8, 9, 10 or 11 and/or can inhibit the binding to a T cell receptor of the said equivalent peptide.

The mycobacterium is generally *M. tuberculosis*. The mycobacterium may be *M. marinum* or *M. kansasii*. The pattern of clinical symptoms can be used to distinguish between these two organisms and *M. tuberculosis*. The mycobacterium may be *M. bovis*. This is able to infect humans.

The T cells which recognise the peptide in the method are generally T cells which have been pre-sensitised in vivo to antigen from a mycobacterium. These antigen-experienced T cells are generally present in the peripheral blood of a host which has been exposed to the mycobacterium at a frequency of 1 in $10^6$ to 1 in $10^3$ peripheral blood mononuclear cells (PBMCs). The T cells may be CD4 and/or CD8 T cells.

It is understood that the term 'peptide' as used herein also includes the analogue of that peptide (which may not be a peptide as defined by the ordinary use of the term) unless the context requires otherwise.

In the method the T cells can be contacted with the peptides in vitro or in vivo, and determining whether the T cells recognise the peptide can be done in vitro or in vivo. Thus the invention provides a method of diagnosis which is practised on the human or animal body. The invention also provides one or more of the peptides or analogues selected from the peptides represented by SEQ ID NO: 5, 6, 7, 8, 9, 10 or 11 and analogues thereof which can bind a T cell receptor that recognises any of the said peptides, but not (a) SEQ ID NO: 3 or 5 or an analogue thereof alone, nor (b) a combination of peptides and/or analogues selected from SEQ ID NO: 3 and 5 and analogues thereof, for use in diagnosing in a host infection by or exposure to a mycobacterium which expresses ESAT-6, said method comprising determining whether T cells of the host recognise the peptide(s) and/or analogue(s).

Determination of whether the T cells recognise the peptide is generally done by detecting a change in the state of the T cells in the presence of the peptide or determining whether the T cells bind the peptide. The change in state is generally caused by antigen specific functional activity of the T cell after the T cell receptor binds the peptide. Generally when binding the T cell receptor the peptide is bound to an MHC class II molecule, which is typically present on the surface of an antigen presenting cell (APC).

The change in state of the T cell may be the start of or increase in secretion of a substance from the T cell, such as a cytokine, especially IFN-γ, IL-2 or TNF-α. Determination of IFN-γ secretion is particularly preferred. The substance can typically be detected by allowing it to bind to a specific binding agent and then measuring the presence of the specific binding agent/substance complex. The specific binding agent is typically an antibody, such as polyclonal or monoclonal antibodies. Antibodies to cytokines are commercially available, or can be made using standard techniques.

Typically the specific binding agent is immobilised on a solid support. After the substance is allowed to bind the solid support can optionally be washed to remove material which is not specifically bound to the agent. The agent/substance complex may be detected by using a second binding agent which will bind the complex. Typically the second agent binds the substance at a site which is different from the site which binds the first agent. The second agent is preferably an antibody and is labelled directly or indirectly by a detectable label.

Thus the second agent may be detected by a third agent which is typically labelled directly or indirectly by a detectable label. For example the second agent may comprise a biotin moiety, allowing detection by a third agent which comprises a streptavidin moiety and typically alkaline phosphatase as a detectable label.

In one embodiment the detection system which is used is the ex-vivo ELISPOT assay described in WO 98/23960. In that assay IFN-γ secreted from the T cell is bound by a first IFN-γ specific antibody which is immobilised on a solid support. The bound IFN-γ is then detected using a second IFN-γ specific antibody which is labelled with a detectable label. Such a labelled antibody can be obtained from MABTECH (Stockholm, Sweden). Other detectable labels which can be used are discussed below.

The change in state of the T cell which can be measured may be the increase in the uptake of substances by the T cell, such as the uptake of thymidine. The change in state may be an increase in the size of the T cells, or proliferation of the T cells, or a change in cell surface markers on the T cell.

Generally the T cells which are contacted in the method are taken from the host in a blood sample, although other types of samples which contain T cells can be used. The sample may be added directly to the assay or may be processed first. Typically the processing may comprise diluting of the sample, for example with water or buffer. Typically the sample is diluted from 1.5 to 100 fold, for example 2 to 50 or 5 to 10 fold.

The processing may comprise separation of components of the sample. Typically mononuclear cells (MCs) are separated from the samples. The MCs will comprise the T cells and APCs. Thus in the method the APCs present in the separated MCs can present the peptide to the T cells. In another embodiment only T cells, such as only CD4 or only CD8 T cells, can be purified from the sample. PBMCs, MCs and T cells can be separated from the sample using techniques known in the art, such as those described in Lalvani et al (1997) J. Exp. Med. 186, p 859-865.

Preferably the T cells used in the assay are in the form of unprocessed or diluted samples, or are freshly isolated T cells (such as in the form of freshly isolated MCs or PBMCs) which are used directly ex vivo, i.e. they are not cultured before being used in the method. However the T cells can be cultured before use, for example in the presence of one or more of the peptides, and generally also exogenous growth promoting cytokines. During culturing the peptides are typically present on the surface of APCs, such as the APC used in the method. Pre-culturing of the T cells may lead to an increase in the sensitivity of the method. Thus the T cells can be converted into cell lines, such as short term cell lines (for example as described in Ota et al (1990) Nature 346, p 183-187).

The APC which is typically present in the method may from the same host as the T cell or from a different host. The APC may be a naturally occurring APC or an artificial APC. The APC is a cell which is capable of presenting the peptide to a T cell. It is typically a B cell, dendritic cell or macrophage. It is typically separated from the same sample as the T cell and is typically co-purified with the T cell. Thus the APC may be present in MCs or PBMCs. The APC is typically a freshly isolated ex vivo cell or a cultured cell. It may be in the form of a cell line, such as a short term or immortalised cell line. The APC may express empty MHC class II molecules on its surface.

Typically in the method the T cells derived from the sample can be placed into an assay with all the peptides (i.e. a pool of the peptides) which it is intended to test (the relevant panel) or the T cells can be divided and placed into separate assays each of which contain one or more of the peptides. Preferably in the in vitro or in vivo forms of the method at least the peptide represented by SEQ ID NO: 1 or an analogue thereof is used. Typically one or more, or all, of the peptides represented by SEQ ID NOs 2, 3, 4, 5 and 6, preferably also 7 and/or 8, and in one embodiment also 9 and/or 10 and/or 111 are also used in the method, leading to the method having an increased sensitivity. In another embodiment only the peptides represented by SEQ ID NOs 1, 2, 3, 4, 5, 6, 8 and 9 are used in the method.

The invention also provides the peptides such as two or more of any of the peptides mentioned herein (for example in any of the combinations mentioned herein) for simultaneous separate or sequential use (e.g. for in vivo use).

In one embodiment peptide per se is added directly to an assay comprising T cells and APCs. As discussed above the T cells and APCs in such an assay could be in the form of MCs. When peptides which can be recognised by the T cell without the need for presentation by APCs are used then APCs are not required. Analogues which mimic the original peptide bound to a MHC molecule are an example of such a peptide.

In one embodiment the peptide is provided to the APC in the absence of the T cell. The APC is then provided to the T cell, typically after being allowed to present the peptide on its surface. The peptide may have been taken up inside the APC and presented, or simply be taken up onto the surface without entering inside the APC.

The duration for which the peptide is contacted with the T cells will vary depending on the method used for determining recognition of the peptide. Typically $10^5$ to $10^7$, preferably $5\times10^5$ to $10^6$ PBMCs are added to each assay. In the case where peptide is added directly to the assay its concentration is from $10^{-1}$ to $10^3$ μg/ml, preferably 0.5 to 50 g/ml or 1 to 10 μg/ml.

Typically the length of time for which the T cells are incubated with the peptide is from 4 to 24 hours, preferably 6 to 16 hours. When using ex vivo PBMCs it has been found that $0.3\times10^6$ PBMCs can be incubated in 10 μg/ml of peptide for 12 hours at 37° C.

The determination of the recognition of the peptide by the T cells may be done by measuring the binding of the peptide to the T cells. Typically T cells which bind the peptide can be sorted based on this binding, for example using a FACS machine. The presence of T cells which recognise the peptide will be deemed to occur if the frequency of cells sorted using the peptide is above a 'control' value. The frequency of antigen-experienced T cells is generally 1 in $10^6$ to 1 in $10^3$, and therefore whether or not the sorted cells are antigen-experienced T cells can be determined.

The determination of the recognition of the peptide by the T cells may be measured in vivo. Typically the peptide is administered to the host and then a response which indicates recognition of the peptide may be measured. In one embodiment the peptide is administered intradermally, typically in a similar manner to the Mantoux test. The peptide may be administered epidermally. The peptide is typically administered by needle, such as by injection, but can be administered by other methods such as ballistics, for example the ballistics techniques which have been used to deliver nucleic acids. EP-A-0693119 describes techniques which can typically be used to administer the peptide. Typically from 0.001 to 1000 μg, for example from 0.01 to 100 μg or 0.1 to 10 μg of peptide is administered.

Alternatively an agent can be administered which is capable of providing the peptides in vivo. Thus a polynucleotide capable of expressing the peptide can be administered, typically in any of the ways described above for the administration of the peptide. The polynucleotide typically has any of the characteristics of the polynucleotide provided by the invention which is discussed below. Peptide is expressed from the polynucleotide in vivo and recognition of the peptide in vivo is measured. Typically from 0.001 to 1000 μg, for example from 0.01 to 100 μg or 0.1 to 10 μg of polynucleotide is administered. Recognition of the peptide in vivo is typically indicated by the occurrence of a DTH response. This is generally measured by visual examination of the site of administration of the peptide to determine the presence of inflammation, such as by the presence of induration, erythema or oedema.

The analogue which can be used in the method can bind to a T cell receptor which recognises the equivalent peptide represented by SEQ ID NO: 1, 2, 3, 4, 5, 6, 7, 8, 9, 10 or 11. Therefore generally when the analogue is added to T cells in the presence of the equivalent said peptide, typically also in the presence of an APC, the analogue inhibits the recognition of the equivalent peptide. The binding of the analogue to the said T cell receptors can be tested by standard techniques. For example T cell receptors can be isolated from T cells which have been shown to recognise the peptide (e.g. using the method of the invention). Demonstration of the binding of the analogue to the T cell receptors can then shown by determining whether the T cell receptors inhibit the binding of the analogue to a substance that binds the analogue, e.g. an antibody to the analogue. Typically the analogue is bound in an MHC molecule in such an inhibition of binding assay.

Typically the analogue inhibits the binding of the peptide to a T cell receptor. In this case the amount of peptide which can bind the T cell receptor in the presence of the analogue is decreased. This is because the analogue is able to bind the T cell receptor and therefore competes with the peptide for binding to the T cell receptor.

T cells for use in the above binding experiments can be isolated from patients with mycobacterial infection, for example with the aid of the method of the invention. Since whole ESAT-6 is unable to bind the T cell receptor which recognises the peptide it is not encompassed by the term 'analogue'.

Other binding characteristics of the analogue are also the same as the peptide, and thus typically the analogue binds to the same MHC class II molecule which the peptide binds. The analogue of the peptide represented by SEQ ID NO: 1 typically binds HLA-DR1 and/or HLA-DR7. The analogue typically binds to antibodies specific for the peptide, and thus inhibits binding of the peptide to such an antibody.

The analogue is typically a peptide. It may have homology with the equivalent original peptide represented by one of SEQ ID NO: 1, 2, 3, 4, 5, 6, 7, 8, 9, 10 or 11. A peptide which is homologous to another peptide is typically at least 70% homologous to the peptide, preferably at least 80 or 90% and more preferably at least 95%, 97% or 99% homologous thereto, for example over a region of at least 15, preferably at least 30, for instance at least 40, 60 or 100 or more contiguous amino acids. Methods of measuring protein homology are well known in the art and it will be understood by those of skill in the art that in the present context, homology is calculated on the basis of amino acid identity (sometimes referred to as "hard homology"). For example the UWGCG Package provides the BESTFIT program which can be used to calculate homology (for example used on its default settings) (Devereux et al (1984) Nucleic Acids Research 12, p 387-395).

The homologous peptides typically differ by substitution, insertion or deletion, for example from 1, 2, 3, 4, 5, 6, 7, 8 or more substitutions, deletions or insertions, which can be at the N or C terminal or at any other position in the sequence. The substitutions are preferably 'conservative'. These are defined according to the following Table. Amino acids in the same block in the second column and preferably in the same line in the third column may be substituted for each other:

| ALIPHATIC | Non-polar | G A P |
| --- | --- | --- |
| | | I L V |
| | Polar-uncharged | C S T M |
| | | N Q |
| | Polar-charged | D E |
| | | K R |
| AROMATIC | | H F W Y |

The analogue is typically from 8 to 80 amino acids in length, such as 10 to 60 or 12 to 50, preferably 15 to 30 or 20 to 25. Typically the amino acids in the analogue at the equivalent positions to amino acids in the original peptide which contribute to binding the MHC molecule or are responsible for the recognition by the T cell receptor, are the same or are conserved.

Typically the analogue peptide comprises one or more modifications, which may be natural post-translation modifications or artificial modifications. The modification may provide a chemical moiety (typically by substitution of a hydrogen, e.g. of a C—H bond), such as an amino, acetyl, hydroxy or halogen (e.g. fluorine) group or carbohydrate group. Typically the modification is present on the N or C terminus.

The analogue may comprise one or more non-natural amino acids, for example amino acids with a side chain different from natural amino acids. Generally, the non-natural amino acid will have an N terminus and/or a C terminus. The non-natural amino acid may be an L-amino acid.

The analogue typically has a shape, size, flexibility or electronic configuration which is substantially similar to the original peptide. It is typically a derivative of the original peptide.

In one embodiment the analogue is or mimics the original peptide bound to a MHC class II molecule. The analogue may be or may mimic the original peptide bound to 2, 3, 4 or more MHC class II molecules associated or bound to each other. These MHC molecules may be bound together using a biotin/streptavidin based system, in which typically 2, 3 or 4 biotin labelled MHC molecules bind to a streptavidin moiety. This analogue typically inhibits the binding of the peptides. Class II complex to a T cell receptor or antibody which is specific for the complex. The analogue is typically an antibody or a fragment of an antibody, such as a Fab or (Fab)$_2$ fragment.

The analogue may be immobilised on a solid support, particularly an analogue which mimics peptide bound to a MHC molecule.

The analogue is typically designed by computational means and then synthesised using methods known in the art. Alternatively the analogue can be selected from a library of compound. The library may be a combinatorial library or a display library, such as a phage display library. The library of compounds may be expressed in the display library in the form of being bound to a MHC class II molecule, such as the MHC molecule which the original peptide binds. Analogues are generally selected from the library based on their ability to mimic the binding characteristics of the original peptides. Thus they may be selected based on ability to bind a T cell receptor or antibody which recognises the original peptide.

The invention also provides a kit for carrying out the method comprising one or more of the peptides or analogues and optionally a means to detect the recognition of the peptide by the T cell. Typically the peptides are provided for simultaneous, separate or sequential use. Typically the means to detect recognition allows or aids detection based on the techniques discussed above.

Thus the means may allow detection of a substance secreted by the T cells after recognition. The kit may thus additionally include a specific binding agent for the substance, such as an antibody. The agent is typically specific for IFN-γ. The agent is typically immobilised on a solid support. This means that after binding the agent the substance will remain in the vicinity of the T cell which secreted it. Thus 'spots' of substance/agent complex are formed on the support, each spot representing a T cell which is secreting the substance. Quantifying the spots, and typically comparing against a control, allows determination of recognition of the peptide.

The kit may also comprise a means to detect the substance/agent complex. A detectable change may occur in the agent itself after binding the substance, such as a colour change. Alternatively a second agent directly or indirectly labelled for detection may be allowed to bind the substance/agent complex to allow the determination of the spots. As discussed above the second agent may be specific for the substance, but binds a different site on the substance than the first agent.

The immobilised support may be a plate with wells, such as a microtitre plate. Each assay can therefore be carried out in a separate well in the plate.

The kit may additionally comprise medium for the T cells, detection agents or washing buffers to be used in the detection steps. The kit may additionally comprise reagents suitable for the separation from the sample, such as the separation of PBMCs or T cells from the sample. The kit may be designed to allow detection of the T cells directly in the sample without requiring any separation of the components of the sample.

The kit may comprise an instrument which allows administration of the peptide, such as intradermal or epidermal administration. Typically such an instrument comprises one or more needles. The instrument may allow ballistic delivery of the peptide. The peptide in the kit may be in the form of a pharmaceutical composition.

The kit may also comprise controls, such as positive or negative Controls. The positive control may allow the detection system to be tested. Thus the positive control typically mimics recognition of the peptide in any of the above methods. Typically in the kits designed to determine recognition in vitro the positive control is a cytokine. In the kit designed to detect in vivo recognition of the peptide the positive control may be antigen to which most individuals should response.

The kit may also comprise a means to take a sample containing T cells from the host, such as a blood sample. The kit may comprise a means to separate mononuclear cells or T cells from a sample from the host.

The invention also provides a peptide with the sequence of SEQ ID NO: 1, 2, 4, 6, 7, 8, 9, 10 or 11 or an analogue thereof. The invention provides a diagnostic product or panel comprising one or more of the peptides typically in the combinations discussed above. The product is typically a composition such as a pharmaceutical composition.

The invention also provides a polynucleotide which is capable of expression to provide a peptide with the sequence of SEQ ID NO: 1, 2, 4, 6, 7, 8, 9, 10 or 11 or an analogue thereof. Typically the polynucleotide is DNA or RNA, and is single or double stranded. The polynucleotide therefore comprises sequence which encodes the sequence of SEQ ID NO: 1, 2, 4, 6, 7, 8, 9, 10 or 11. To the 5' and 3' of this coding sequence the polynucleotide of the invention has sequence or codons which are different from the sequence or codons 5' and 3' to these sequences in the ESAT-6 gene. Therefore the polynucleotide of the invention does not comprise the sequence coding for the whole of ESAT-6 or fragments of ESAT-6, other than sequence coding for fragments represented by SEQ ID NO: 1, 2, 4, 6, 7, 8, 9, 10 or 11.

5' and/or 3' to the sequence encoding the peptide the polynucleotide has coding or non-coding sequence. Sequence 5' and/or 3' to the coding sequence may comprise sequences which aid expression, such as transcription and/or translation, of the sequence encoding the peptide. The polynucleotide may be capable of expressing the peptide in a prokaryotic or eukaryotic cell. In one embodiment the polynucleotide is capable of expressing the peptide in a mammalian cell, such as a human, primate or rodent cell.

The polynucleotide may be incorporated into a replicable vector. Such a vector is able to replicate in a suitable cell. The vector may be an expression vector. In such a vector the polynucleotide of the invention is operably linked to a control sequence which is capable of providing for the expression of the polynucleotide. The vector may contain a selectable marker, such as the ampicillin resistance gene.

The polynucleotide, peptide or antibody (see below) of the invention, or the agents used in the method (for example in the detection of substances secreted from T cells) may carry a detectable label. Detectable labels which allow detection of the secreted substance by visual inspection, optionally with the aid of an optical magnifying means, are preferred. Such a system is typically based on an enzyme label which causes colour change in a substrate, for example alkaline phosphatase causing a colour change in a substrate. Such substrates are commercially available, e.g. from BIORAD. Other suitable labels include other enzymes such as peroxidase, or protein labels, such as biotin; or radioisotopes, such as $^{32}$p or $^{35}$S. The above labels may be detected using known techniques.

Polynucleotides, peptides or antibodies (see below) of the invention may be in substantially purified form. They may be in substantially isolated form, in which case they will generally comprise (for example about or at least) 90%, such as (for example about or at least) 95, 97 or 99% of the polynucleotide, peptide or antibody in the preparation. The substantially isolated peptides which are not peptides (as defined in the normal sense of the word) generally comprise (for example about or at least) 90%, such as (for example about or at least) 95, 97 or 99% of the dry mass of the preparation. The polynucleotide or peptide are typically substantially free of other cellular components or substantially free of other mycobacterial cellular components. The polynucleotide or peptide may be used in such a substantially isolated, purified or free form in the method or be present in such forms in the kit.

The peptide or any combination of the peptides (for example as mentioned here) is provided for use in a method of diagnosis practised on the human or animal body. The combinations of peptides are provided for simultaneous, separate or sequential use in such a method.

The peptide or polynucleotide may be in the form of a pharmaceutical composition which comprises the peptide or polynucleotide and a pharmaceutically acceptable carrier or diluent. Suitable carriers and diluents include isotonic saline solutions, for example phosphate-buffered saline. Typically the composition is formulated for intradermal or epidermal administration or for application by ballistic techniques. Thus the peptide or polynucleotide may be associated with a carrier particle for ballistic delivery.

The peptide of the invention can be made using standard synthetic chemistry techniques, such as by use of an automated synthesizer.

The peptide is typically made from a longer polypeptide e.g. a fusion protein, which polypeptide typically comprises the sequence of the peptide. The peptide may be derived from the polypeptide by for example hydrolysing the polypeptide, such as using a protease; or by physically breaking the polypeptide. The polypeptide is typically ESAT-6, which may have been expressed recombinantly.

The peptide can also be made in a process comprising expression of a polynucleotide, such as by expression of the polynucleotide of the invention. The expressed polypeptide may be further processed to produce the peptide of the invention. Thus the peptide may be made in a process comprising cultivating a cell transformed or transfected with an expression vector as described above under conditions to provide for expression of the peptide or a polypeptide from which the peptide can be made. The polynucleotide of the invention can be made using standard techniques, such as by using a synthesiser.

The invention also provides use of a peptide or analogue of the invention to produce an antibody specific to the peptide. This antibody or any of the antibodies mentioned herein may be produced by raising antibody in a host animal. Such antibodies will be specific to the peptide or to the substances mentioned above which bind antibodies. The peptide or substances are referred to as the 'immunogen' below. Methods of producing monoclonal and polyclonal antibodies are well-known. A method for producing a polyclonal antibody comprises immunising a suitable host animal, for example an experimental animal, with the immunogen and isolating immunoglobulins from the serum. The animal may therefore be inoculated with the immunogen, blood subsequently removed from the animal and the IgG fraction purified. A method for producing a monoclonal antibody comprises immortalising cells which produce the desired antibody. Hybridoma cells may be produced by fusing spleen cells from an inoculated experimental animal with tumour cells (Kohler and Milstein (1975) Nature 256, 495-497).

An immortalized cell producing the desired antibody may be selected by a conventional procedure. The hybridomas may be grown in culture or injected intraperitoneally for formation of ascites fluid or into the blood stream of an allogenic host or immunocompromised host. Human antibody may be prepared by in vitro immunisation of human lymphocytes, followed by transformation of the lymphocytes with Epstein-Barr virus.

For the production of both monoclonal and polyclonal antibodies, the experimental animal is suitably a goat, rabbit, rat or mouse. If desired, the immunogen may be administered as a conjugate in which the immunogen is coupled, for example via a side chain of one of the amino acid residues, to a suitable carrier. The carrier molecule is typically a physiologically acceptable carrier. The antibody obtained may be isolated and, if desired, purified.

The invention is illustrated by the following Examples:

Example 1

The Subjects Studied

Patients and controls were recruited prospectively at Northwick Park and St Mark's NHS Trust, London, and the hospitals of the Oxford Radcliffe NHS Trust, Oxford, over a 16 month period from October 1997. A single heparinised blood sample was drawn from each subject.

Patients with compatible clinical and radiographic findings who were bacteriologically confirmed with positive cultures for *M. tuberculosis* from one or more clinical specimens were recruited as tuberculosis cases. 29/47 patients (62%) were either untreated at the time of venesection or had received less than one month's therapy; the remainder were at later time points in their treatment course.

Control patients were group-matched for ethnicity, age (within 4 years) and sex, and comprised individuals with a wide range of infectious, inflammatory, granulomatous, autoimmune and neoplastic conditions (table 4). These included diseases that can be clinically difficult to differentiate from tuberculosis and others which, like tuberculosis, can present as pyrexia of unknown origin. Patients with a past history of tuberculosis and those who reported recent contact with a known case of tuberculosis were excluded. None of the tuberculosis or control patients had any clinical features to suggest HIV infection.

Example 2

Results Using the ELISPOT Assay

The ELISPOT assay was used to detect ex vivo antigen-experienced CD4 T cells specific for ESAT-6. 17 peptides spanning the length of the ESAT-6 molecule were synthesised by solid-phase f-moc chemistry (RESEARCH GENETICS, Alabama, USA and ZINSSER ANALYTICAL Frankfurt, Germany). Each peptide was 15 amino acids in length and overlapped its adjacent peptide by 10 residues. Identity was confirmed by mass spectrometry and purity by high performance liquid chromatography. Eight peptides were frequently recognised epitopes; every subject who responded to any of the 17 ESAT-6-derived peptides also responded to at least one of the panel of 8 peptides represented by SEQ ID NOs 1 to 8. Sequence homology searches of the SWISSPROT and translated GENBANK databases of all known protein sequences confirmed that the sequences of these peptides are uniquely restricted to the ESAT-6 protein of *M. tuberculosis* complex. A response to one or more of the peptides in this panel, tested individually, was scored as indicative of *M. tuberculosis* infection.

Patients were also found to respond to the peptides represented by SEQ ID NOs 9 to 11.

Ex Vivo ELISPOT Assay for Single Cell IFN-γ Release: Enumeration of Circulating ESAT-6 Peptide-Specific T Cells from Peripheral Blood Based on the principle of a sandwich capture ELISA, the ELISPOT assay captures and detects IFN-γ molecules in the immediate vicinity of the T cell from which they are secreted, while still at a relatively high concentration. Following development, each resulting spot thus represent the "footprint" of an individual antigen-specific IFN-γ-secreting T cell, or spot-forming cell (SFC). The ex vivo ELISPOT assay for IFN is sufficiently sensitive to detect antigen-specific T cells directly from peripheral blood without the need for a prior in vitro stimulation step (Lalvani et al (1997) J. Exp. Med. 186 p 859-865). Moreover, since the ex vivo ELISPOT assay enumerates antigen-specific T cells with rapid effector function, only short incubation periods are required.

Peripheral blood mononuclear cells (PBMC) were separated from 12 mls blood by standard means as described in Lalvani et al (see above) and suspended in RPMI supplemented with L-glutamine 2 mM, penicillin 100 μg/ml and 10% heat inactivated foetal calf serum (SIGMA, St. Louis, Mo., USA) (R10).

Ninety-six-well polyvinylidene difluoride (PVDF)-backed plates (MILLIPORE) precoated with the anti-IFN-γ mAB 1-D1K at 15 μg/ml (MABTECH, Stockholm) were washed with RPMI medium 1640 and blocked with R10 for 1 hr at room temperature.

$3 \times 10^5$ PBMC were added in 100 μl RIO/well to the pre-coated plates and peptides were added individually to each well at a final concentration 10 μg/ml. PPD (Batch RT49, STATENS SERUM INSTITUT, Copenhagen, Denmark) was also added at 20 μg/ml. Phytohaemagglutinin (ICN BIO-MEDICALS, Aurora, Ohio, USA) at 5 μg/ml was added to positive control wells and no peptide was added to the negative control wells. Additionally, whole recombinant ESAT-6 was added at 10 μg/ml for 17 tuberculosis patients and patients and all controls.

Assays were incubated for 6-12 hrs at 37° C., 5% CO and arrested by washing×6 with PBS 0.05% Tween-20 (SIGMA, St. Louis, Mo., USA). Next, 100 μl of 1 μg/ml of the biotinylated anti-IFN-γ mAb 7-B6-1-biotin (MABTECH, Stockholm, Sweden) was added. After 2 hrs incubation at room temperature, plates were washed again ×6 and a 1:1000 dilution of streptavidin-alkaline phosphate conjugate (MABTECH, Stockholm, Sweden) was added to the wells and the plates incubated for a further hour. Next, wells were again washed ×6 and 100 μl of chromogenic alkaline phosphatase substrate (BIORAD, Hercules, Calif., USA), diluted 1:25 with deionized water, was added. After 30 mins the colorimetric reaction was terminated by washing with tap water and plates allowed to dry.

Responses were scored as positive only if the test well contained at least 5 IFN-γ SFCs more than the negative control wells and additionally this number was at least twice that in negative control wells. This cut-off point (5 IFN-γ SFCs per $3 \times 10^5$ PBMC) translates into a lower threshold of detection of 17 peptide-specific T cells per million PBMC, or 1/59,000 PBMC. Although the person performing the assays was not blind to the tuberculosis status of the patients, the read-out in SFCs is quantitative, our criteria for a positive response were stringent and background numbers of SFCs in the negative control wells were always below 3, so that positive responses were objective and clear-cut. In all cases, positive and negative responses were immediately recognisable by direct inspection of the plate, prior to precise enumeration with a magnifying glass.

The accuracy of the ESAT-6 peptide-based test as applied to the diagnosis of active tuberculosis was calculated and expressed as sensitivity, specificity (confidence intervals calculated from the standard binomial) and as likelihood ratios.

The latter were then applied to a typical clinical scenario where tuberculosis is considered a diagnostic possibility with a pre-test probability of 20%.

Pools of peptides were also used in the above assays and were found to be as effective in detecting responses as the same peptides tested individually in separate assays.

Example 3

Demographic and Clinical Features of Patients and Controls

The tuberculosis patients represent the broad ethnic mix characteristic of tuberculosis in the UK, with a high prevalence of disease amongst persons from the Indian Subcontinent (ISC) and blacks (table 2). The control patients were closely matched for ethnic origin, age and sex ratio (table 2) and their diagnoses are listed in table 4. The tuberculosis patients are representative of the broad clinical spectrum of disease caused by M. tuberculosis and 22/47 had extrapulmonary tuberculosis (table 3). Of those with pulmonary tuberculosis, 6/25 were sputum smear negative for acid fact bacilli. Thus immediate presumptive diagnosis by sputum microscopy was not possible in 28/47 (60%) of patients.

Prompt Diagnosis of M. tuberculosis Infection by Detection of ESAT-6-Specific T Cells in Blood 45/47 (96%) tuberculosis patients responded to one or more of the panel of 8 peptides shown in table 1 in the ex vivo ELISPOT assay for IFN-γ (table 5). An unusually high proportion of patients responded to ES1. The inventors have shown that this peptide binds HLA DR1 and DR7.

Frequencies of ESAT-6 peptide-specific IFN-γ-secreting T cells were generally high, with a median of 200 ESAT-6 peptide-specific T cells per million PBMC (inter-quartile range 105-596). IFN-γ SFCs specific for each of the 8 peptides in table 1 are mainly CD4 T cells because T cell lines have been generated against each of these peptides in vitro and peptide-specific responses were abrogated by specific immunomagnetic depletion of CD4 T cells. ESAT-6-specific CD8 T cells are also detected by peptides in the panel (e.g. ES14) that contain CD8 epitopes.

Only 4/47 (8.5%) controls with non-tuberculous illnesses responded to one or more of the panel of 8 ESAT-6-derived peptides; frequencies of peptide-specific IFN-γ-secreting T cells in these 4 responders were similar to those seen in tuberculosis patients. In all remaining controls there was a complete lack of response to all peptides. Use of the expanded set of 17 peptides spanning the entire length of ESAT-6 gave identical results to those observed with the panel of 8 broadly immunogenic epitopes.

The 2 non-responders were pulmonary tuberculosis patients with advanced disease and both were tested prior to treatment. Their clinical details are reviewed in the discussion. Of the 4 controls who responded, 2 had acute pneumonia, one had acute bronchitis and the fourth had cellulitis. All 4 patients also had a strong ex vivo response to PPD in the ELISPOT assay for IFN-γ, indicating that they were sensitised to tuberculin.

Comparison of ESAT-6-Specific T Cell Responses with Responses to PPD 26 tuberculosis patients underwent tuberculin skin testing with intradermal inoculation of 1 TU of PPD (NHS supply). Cutaneous induration at 72 hrs was measured with a ruler, and induration of 5 mm or more in diameter was taken as positive, as per convention. Of these patients, only 18 (69%) had a positive result on TST. By comparison, one third more, 24/26 (92%), were positive by ex vivo ELISPOT for IFN-γ and, overall, 45/47 (96%) had a positive response by ex vivo ELISPOT (p=0.002, Fisher's exact test). Although the control patients did not undergo tuberculin skin testing, 26/47 (55%) had positive responses to PPD in the ex vivo ELISPOT assay for IFN-γ, indicating prior in vivo sensitisation of their CD4 T cells to antigens in PPD.

Clinical Utility of the ESAT-6 Peptide-Based ELISPOT Assay for IFN-γ

The operational characteristics of this assay in this study are shown in table 5. These likelihood ratios generate large changes from pre-test to post-test probability. For example, if applied to a hypothetical patient where tuberculosis is considered a diagnostic possibility with a pre-test probability of 20%, a positive test result would confer a positive predictive value of 74% while a negative test result would give a negative predictive value of 1%.

Discussion

We have developed a highly accurate blood test for the rapid detection of M. tuberculosis infection. The success of this ex vivo assay is based on the sensitive detection of antigen-specific T cells using a highly immunogenic antigen that is highly specific for M. tuberculosis. When applied as a diagnostic test for bacteriologically confirmed active tuberculosis, this assay yields a sensitivity of 96% and a specificity of 91.5% in the patient population studies (table 5). The tuberculosis patients represent a broad ethnic mix, reflecting the epidemiology of tuberculosis in the UK and, among the ethnically matched control patients, there were many common diseases that can be difficult to distinguish from tuberculosis. The operational characteristics (table 5) of this assay are therefore likely to be generally applicable to clinical practice in the UK. The test requires a single venous blood sample, is easy and quick to perform, needs no specialised laboratory facilities and generates results by the next day; it is thus potentially well suited to routine hospital laboratories and could be readily automated.

The TST and sputum microscopy for AFB are the only tests for immediate presumptive diagnosis of tuberculosis in general use. The sensitivity of the TST among the 26 tuberculosis patients who were tested by this method was only 69%, significantly less than the 96% sensitivity of the ESAT-6-based ex vivo ELISPOT (p=0.002). Given the multiple major limitations or the TST, the ex vivo ELISPOT assay appears to be a superior means of rapidly detecting M. tuberculosis infection. In our series of patients, sputum microscopy would have detected only 40% of cases, compared with 96% for the ex vivo ELISPOT, which also detected all 6 cases of sputum smear negative pulmonary tuberculosis. Furthermore, sputum microcopy cannot differentiate between M. tuberculosis and atypical mycobacteria. Since the esat-6 gene is restricted to M. tuberculosis complex, M. kansasii, M. marinum and M. szulgei, (of these only M. kansasii can cause disease clinically similar to tuberculosis) our ESAT-6-based test may prove to be more specific than sputum microscopy.

A variety of blood tests aimed at diagnosing tuberculosis have been developed in the past but none have proved sufficiently sensitive, specific and convenient to enter routine use. Serological assays have suffered from the lack of a target antigen that is as species-specific as ESAT-6 and the sensitivity of these assays is generally disappointing, especially in acute forms of tuberculosis (pulmonary, miliary and pleural). PCR of circulating M. tuberculosis complex DNA in PBMC has been investigated as a method for diagnosing tuberculosis. For pulmonary tuberculosis, sensitivity ranges from 33%-95% for different investigators; in the largest series, of 76 bacteriologically confirmed HIV negative patients, sensitivity was 41%-27%. For extrapulmonary tuberculosis, blood based PCR had a sensitivity of only 4-27%.

2/47 tuberculosis patients did not respond in the ex vivo ELISPOT assay. Both were pulmonary tuberculosis patients with advanced disease and had been severely symptomatic for several months prior to diagnosis and both were cachectic. One, a 20 year old Asian man, had extensive sputum smear positive cavitatory disease with pleural involvement and was anergic on TST; the other, a 22 year old African woman, was sputum smear negative, had a bronchopneumonic pattern radiographically and was positive on TST. Interestingly, both patients were lymphopaenic, but both were HIV-negative and responded well to therapy. Chronic, advanced tuberculosis causes non-specific immunosupression which might conceivably account for the lack of detectable ESAT-6-specific IFN-γ-secreting T cells in these patients, but for all four patients with severe miliary disease, often associated with cutaneous anergy, nonetheless responded in the ex vivo ELISPOT assay. At present it is unclear why these two patients did not respond and they represent true false negatives.

Although 33/47 (70%) control patients with non-tuberculosis illnesses were BCG-vaccinated (as indicated by the presence of a scar), only 4/47 responded in the ex vivo ELISPOT assay and 3 of these were not BCG-vaccinated. This assay is thus the first to successfully distinguish between BCG-vaccinated and M. tuberculosis infected patients. None of the 4 control patients who responded had clinical or radiographic features suggestive of tuberculosis; two had acute pneumonia, one had acute bronchitis and one cellulitis; all responded to first-line antibiotics. All 4 patients also had a strong ex vivo response to PPD in the ELISPOT assay for IFN-γ, indicating that they were sensitised to tuberculin. Importantly, all four were from countries of high endemicity for tuberculosis; three were Asian immigrants to the UK from Kenya (and all return there regularly) and the fourth was a visitor from Ethiopia. Thus all four had significant risk factors for exposure to M. tuberculosis. In contrast, none of the 22 control patients who were born in the UK gave a positive response. It likely that the 4 responders were, in fact, infected with M. tuberculosis but clearly do not have active disease. Thus, although these responders represent false positives if the assay is applied as a diagnostic test of active tuberculosis, we believe that they are, in biological terms true positives, since the test has correctly detected M. tuberculosis infection. Unfortunately, this conclusion cannot be formally proven since there exists no definitive means of confirming subclinical M. tuberculosis infection in asymptomatic exposed contacts. In contrast to the ESAT-6 peptides, ex vivo ELISPOT responses to PPD were common (26/47) throughout the control group, indicating prior in vivo sensitisation of their CD4 T cells to antigens in PPD, probably as a result of BCG vaccination or exposure to environmental mycobacteria.

Further studies will be needed to answer whether the ESAT-6 based ex vivo ELISPOT maintains its high sensitivity and specificity in other settings. In tuberculosis-endemic countries, where a significant proportion of healthy individuals are latently infected with Ad tuberculosis, the specificity of an assay based on the detection of an M. tuberculosis-sensitised cellular immune system might be lower than in this study. However, the high sensitivity of the ex vivo ELISPOT means that it could still be used to rule out a diagnosis of tuberculosis. The assay will also need to be validated in children, where tuberculosis is usually a primary infection and presents acutely; animal studies of ESAT-6-specific cellular immune responses indicate that ESAT-6 is especially strongly recognised in the early phase of primary infection, suggesting that our assay should prove as effective in children as it is in adults. Finally, the ex vivo ELISPOT needs to be evaluated in a separate study of HIV-infected tuberculosis patients.

Example 4

Detection of CD4 T Cell Responses in Healthy Contacts

The panel consisting of the peptides shown by SEQ ID Nos: 1 to 8 was used to detect responses in 26 healthy household contacts of index cases with sputum smear positive pulmonary tuberculosis. Responses were detected in 22 of the contacts indicating that the panel was sensitive enough to detect asymptomatic M. tuberculosis infection.

26 healthy volunteers (22 of whom were BCG vaccinated) were also tested and none responded to any of the peptides. Thus the panel was able to successfully distinguish between asymptomatic infected contacts and healthy BCG vaccines.

Example 5

Detection of CD4 T Cell Responses in Healthy Contacts Using a Different Panel

A different panel than the one used in the previous Examples was used to detect responses in healthy contacts using the ELISPOT assay. The panel consisted of the peptides shown by SEQ ID Nos: 1 to 6, 8 and 9.

All contacts have prolonged exposure to an index case with smear positive open pulmonary tuberculosis and have a positive Heaf test of grade 3 or 4. One of the contacts works in the same room (and on the same shift) as an index at a factory. One contact was on the same hospital ward as the index for several days. All other contacts were from the same household as the index.

20 out of 22 contacts tested positive with the panel. 15 of the contacts tested positive with ES1.

Example 6

Sensitivity of the Panel in Comparison with the Use of Whole ESAT-6

A number of patients with tuberculosis were found to only have CD8 T cell responses specific for ESAT-6, and no CD4 T cell responses for this antigen. Since in a diagnostic test whole ESAT-6 will only elicit a response from CD4 T cells and not from CD8 T cells such patients (who only have CD8 T cell responses) could not be detected using a diagnostic test based on whole ESAT-6. However peptides are able to elicit a response from both CD4 and CD8 T cells and therefore those patients could detected using the peptides of the invention. Thus the use of such peptides leads to a higher sensitivity of diagnostic test.

TABLE 1

| Peptide | % of TB patients responding to individual peptide |
|---|---|
| ES1 | 57 |
| ES2 | 40 |
| ES4 | 23 |
| ES7 | 15 |
| ES11 | 34 |
| ES12 | 25 |
| ES14 | 28 |
| ES15 | 34 |

TABLE 2

Demographic characteristics of tuberculosis patients and controls with non-tuberculosis illnesses

|  |  | Tuberculosis Patients (%) | Controls with non-TB illnesses (%) |
|---|---|---|---|
| Ethnicity: | ISC | 24 (51) | 24 (48) |
|  | Black | 14 (30) | 14 (28) |
|  | White | 8 (17) | 9 (19) |
|  | Oriental | 1 (2) | 0 (0) |
| Total: |  | 47 | 47 |
| Sex (M/F) |  | 30/17 | 27/20 |
| Age: mean (range) |  | 35 (18-74) | 39 (17-75) |

ISC* = Indian Subcontinent

TABLE 3

Clinical features of tuberculosis patients
(all confirmed culture positive for *M. tuberculosis*)

|  | No. of patients (%) |
|---|---|
| Pulmonary TB (PTB) | 25 |
| Sputum smear negative | 6 (13) |
| Sputum smear positive | 19 (40) |
| Positive TST/Total no. of PTB patients tested | 9/14 |
| Extrapulmonary TB (EPTB) | 22 |
| Lymphadenitis | 6 (13) |
| Muskuloskeletal | 6 (13) |
| Miliary | 3 (6) |
| Gastrointestinal | 3 (6) |
| Pleural | 3 (6) |
| Meningeal & miliary | 1 (2) |
| Positive TST/Total no. of EPTB patients tested | 9/12 |
| Overall positive TST/all PTB and EPTB patients tested | 18/26 (69%) |

TABLE 4

Diagnosis of controls with non-TB illnesses

| Diagnosis | No. of patients |
|---|---|
| Pneumonia | 6 |
| Sarcoidosis | 3 |

TABLE 4-continued

Diagnosis of controls with non-TB illnesses

| Diagnosis | No. of patients |
|---|---|
| Infective Endocarditis | 3 |
| Lymphoma | 2 |
| Lung cancer | 2 |
| Chronic osteomyelitis | 2 |
| Ulcerative colitis | 2 |
| Crohn's disease | 2 |
| Infective enterocolitis | 2 |
| Malaria (*P. falciparum, P. vivax*) | 2 |
| Chronic Liver Disease | 2 |
| Cellulitis | 2 |
| Haemaglobinopathies (SS, HbH) | 2 |
| Pulmonary *A. lumbridoides* infection | 1 |
| Acute pancreatitis | 1 |
| Dengue fever | 1 |
| Bladder schistosomiasis | 1 |
| SLE | 1 |
| Acute bronchitis | 1 |
| Meningococcaemia | 1 |
| Tonsillitis | 1 |
| Sickle cell criais | 1 |
| Gastric ulcer | 1 |
| Dermatitis Herpetiformis | 1 |
| Venous thrombosis | 1 |
| Nephrotic syndrome | 1 |
| Congestive cardiac failure | 1 |

TABLE 5

Projected clinical usefulness of ex vivo ELISPOT with ESAT-6 peptides for the diagnosis of active tuberculosis, based on its operational characteristics in this study

| Response Rates |  |
|---|---|
| TB Patients | 45/47 |
| Controls with non-TB illness | 4/47 |
| Sensitivity (95% Cl) | 96% (92%-100%) |
| Specificity (95% Cl*) | 91.5% (86%-97%) |
| Likelihood Ratios (LR) |  |
| Positive LR | 11.25 |
| Negative LR | 0.05 |

Cl* = Confidence Interval

---

We claim:

1. A method of diagnosing infection in a human host by, or exposure of a human host to, a mycobacterium which expresses ESAT-6, which method comprises the steps of:
    (i) contacting a population of T cells from the host with the peptide represented by SEQ ID NO: 1; and
    (ii) determining in vitro whether the T cells of said T cell population show a recognition response to said peptide.

2. The method of claim 1, further comprising contacting said population of T cells with one or more peptides selected from the group consisting of: a peptide represented by SEQ ID NO:2, a peptide represented by SEQ ID NO:3, a peptide represented by SEQ ID NO:4, a peptide represented by SEQ ID NO:5, a peptide represented by SEQ ID NO:6, a peptide represented by SEQ ID NO:7, a peptide represented by SEQ ID NO:8, a peptide represented by SEQ ID NO:9, a peptide represented by SEQ ID NO:10, and a peptide represented by SEQ ID NO:11.

3. The method of claim 1, further comprising contacting said population of T cells with a peptide represented by SEQ ID NO:2.

4. The method of claim 1, further comprising contacting said population of T cells with a peptide represented by SEQ ID NO:3.

5. The method of claim 1, further comprising contacting said population of T cells with a peptide represented by SEQ ID NO:4.

6. The method of claim 1, further comprising contacting said population of T cells with a peptide represented by SEQ ID NO:5.

7. The method of claim 1, further comprising contacting said population of T cells with a peptide represented by SEQ ID NO:6.

8. The method of claim 1, further comprising contacting said population of T cells with a peptide represented by SEQ ID NO:7.

9. The method of claim 1, further comprising contacting said population of T cells with a peptide represented by SEQ ID NO:8.

10. The method of claim 1, further comprising contacting said population of T cells with a peptide represented by SEQ ID NO:9.

11. The method of claim 1, further comprising contacting said population of T cells with a peptide represented by SEQ ID NO:10.

12. The method of claim 1, further comprising contacting said population of T cells with a peptide represented by SEQ ID NO:11.

13. The method of claim 1, wherein the T cells are freshly isolated.

14. The method of claim 1, wherein the T cells are isolated from blood.

15. The method of claim 1, wherein the T cell population comprises CD4 and CD8 T cells.

16. The method of claim 1, wherein the host is a healthy human host who has been exposed to the mycobacterium.

17. A kit for diagnosing infection in a human host by, or exposure of a human host to, a mycobacterium that expresses ESAT-6, comprising a peptide represented by SEQ ID NO: 1.

18. The kit of claim 17, further comprising an apparatus to detect recognition of the peptide by a T cell population.

19. The kit of claim 17, wherein the kit further comprises one or more peptides selected from the group consisting of: a peptide represented by SEQ ID NO:2, a peptide represented by SEQ ID NO:3, a peptide represented by SEQ ID NO:4, a peptide represented by SEQ ID NO:5, a peptide represented by SEQ ID NO:6, a peptide represented by SEQ ID NO:7, a peptide represented by SEQ ID NO:8, a peptide represented by SEQ ID NO:9, a peptide represented by SEQ ID NO:10, and a peptide represented by SEQ ID NO:11.

* * * * *